US008574582B2

(12) United States Patent (10) Patent No.: US 8,574,582 B2
Branigan et al. (45) Date of Patent: Nov. 5, 2013

(54) METHODS FOR MEDIATING FIBROTIC RESPONSE

(75) Inventors: Patrick Branigan, Radnor, PA (US); Jason Ekert, Radnor, PA (US)

(73) Assignee: Janssen Biotech, Inc., Horsham, PA (US)

( * ) Notice: Subject to any disclaimer, the term of this patent is extended or adjusted under 35 U.S.C. 154(b) by 431 days.

(21) Appl. No.: 12/606,575

(22) Filed: Oct. 27, 2009

(65) Prior Publication Data

US 2010/0111968 A1 May 6, 2010

Related U.S. Application Data

(60) Provisional application No. 61/110,127, filed on Oct. 31, 2008.

(51) Int. Cl.
*A61K 39/395* (2006.01)
*A61K 38/02* (2006.01)
*A61P 37/00* (2006.01)
*A61P 17/00* (2006.01)

(52) U.S. Cl.
USPC .................. 424/158.1; 514/1.1; 514/19.3

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 6,562,578 B1 | 5/2003 | Gorman et al. | |
| 6,635,443 B1 | 10/2003 | Shi et al. | |
| 8,206,717 B2 * | 6/2012 | McKenzie et al. | 424/158.1 |
| 2006/0078967 A1 | 4/2006 | Medlock et al. | |
| 2007/0020735 A1 | 1/2007 | Chen et al. | |
| 2007/0071675 A1 | 3/2007 | Wu et al. | |

FOREIGN PATENT DOCUMENTS

WO WO2009/039310 A2 3/2009

OTHER PUBLICATIONS

Phillips, A., J Pharm Pharmacology, 2001, vol. 53, pp. 1169-1174.*
Pirollo et al. Cancer Research, 2008, vol. 68, No. 5, pp. 1247-1250.*
Vidal et al. European Journal of Cancer, 2005, vol. 41, pp. 2812-2818.*
Abe et al, "*Peripheral Blood Fibrocytes: Differentiation Pathway and Migration to Wound Sites*", Journal of Immunology, 166: 7556-7562 (2001).
Abe et al, *Cells Derived from the Circulation Contribute to the Repair of Lung Injury*, American Journal of Respiratory and Critical Care Medicine, 170: 1158-1163 (2004).
Angkasekwinai, et al., "*Interleukin 25 promotes the initiation of proallergic type 2 responses,*" Journal of Experimental Medicine, 204(7): 1509-1517 (2007).
Ballantyne, et al., "*Blocking IL-25 prevents airway hyperresponsive in allergic asthma,*" Journal of Allergy and Clinical Immunology, 120: 1324-1331 (2007).
Barth, et al., "*CD34+ fibrocytes in invasive ductal carcinoma, ductal carcinoma in situ, and benign breast lesions,*" Virchows Archives, 440: 298-303 (2002).
Bellini and Mattoli., "*The role of the fibrocyte, a bone marrow-derived mesenchymal progenitor, in reactive and reparative fibroses*", Laboratory Investigations, 87: 858-870 (2007).
Bucala et al, "*Circulating Fibrocytes Define a New Leukocyte Subpopulation that Mediates Tissue Repair*", Molecular Medicine, 1(1): 71-81 (1994).
Cai et al, "*Pathways by Which Interleukin 17 Induces Articular Cartilage Breakdown In Vitro and In Vivo*", Cytokine, 16(1): 10-21 (2001).
Chauhan et al, "*There is more than one kind of myofibroblast: anlaysis of CD34 expression in benign, in situ, and invasive breast lesions*", Journal of Clinical Pathology, 56: 271-276 (2003).
Chesney et al, "*Regulated Production of Type 1 Collagen and Inflammatory Cytokines by Peripheral Blood Fibrocytes*", Journal of Immunology, 160: 419-425 (2006).
Chesney et al, "*Peripheral Blood Fibrocytes: Mesenchymal Precursor Cells and Pathogenesis of Fibrosis*" Current Rheumatology Reports, 2: 501-505 (2000).
Crouch et al, "*Pathobiology of pulmonary fibrosis*", American Journal of Physiology, Lung and Cell Molecular Physiology, 259: L159-L184 (1990).
Epperly et al, "*Bone Marrow Origin of Myofibroblasts in Irradiation Pulmonary Fibrosis*", American Journal of Respiratory, Cellular and Molecular Biology, 29: 213-224 (2003).
Fallon et al, "*Identification of an interleukin (IL)-25-dependent cell population that provides IL-4, IL-5, and IL-13 at the onset of helminth expulsion*", Journal of Experimental Medicine, 203(4): 1105-1116 (2006).
Fichtner-Feigl, et al., Induction of IL-13 Triggers TGF-beta1-Dependent Tissue Fibrosis in Chronic 2,4,6-Trinitrobenzene Sulfonic Acid Colitis, The Journal of Immunology, 178: 5859-5870 (2007).
Fishwild et al, "*High-avidity human IgGk monoclonal antibodies from a novel strain of minilocus transgenic mice*", Nature Biotechnology, 14: 845-851 (1996).
Floer et al, "*Role of MutS homolog 2 (MSH2) in intestinal myofibroblast proliferation during Crohn's disease stricture formation*", American Journal of Physiology and Gastrointestinal and Liver Physiology, 295: G581-G590 (2008).
Ford, et al., "Characterization of Wound cytokines in the Sponge Matrix Model," Archives of Surgery, 124: 1422-1428 (1989).
Fort et al., "*IL-25 Induces IL-4, IL-5 and IL-13 and Th2-Associated Pathologies in Vivo*", Immunity, 15: 985-995 (2001).
Freudenthal and Steinman, "*The distinct surface of human blood dendritic cells, as observed after an improved isolation method*", Proceedings of the National Academy of Science, USA, 87: 7698-7702 (1990).
Frid et al, "*Hypoxia-Induced Pulmonary Vascular Remodeling Requires Recruitment of Circulating Mesenchymal Precursors of a Monocyte/Macrophage Lineage*" American Journal of Pathology, 168: 659-669 (2006).
Gomperts and Stierter, "*Fibrocytes in lung disease*", Journal of Leukocyte Biology, 82: 449-456 (2007).

(Continued)

*Primary Examiner* — Bridget E Bunner
*Assistant Examiner* — Fozia Hamud
(74) *Attorney, Agent, or Firm* — Kirk Baumeister (57) ABSTRACT

Methods for mediating fibrotic response by modulating IL-25 signaling in fibrocytes are disclosed.

4 Claims, 8 Drawing Sheets

(56) References Cited

OTHER PUBLICATIONS

Gratchev et al, "*The Receptor for Interleukin-17E is Induced by Th2 Cytokines in Antigen-Presenting Cells*", Journal of Immunology, 60: 233-237 (2004).
Hartlapp, et al., "Fibrocytes induce an angiogenic phenotype in cultured endothelial cells and promote angiogenesis in vivo," FASEB Journal, 15: 2215-2224 (2001).
Hashimoto et al, "*Bone Marrow—derived progenitor cells in pulmonary fibrosis*", Journal of Clinical Investigation, 113(2): 243-252 (2004).
Haudek et al, "*Bone marrow-derived fibroblast precursors mediate ischemic cardiomyopathy in mice*", Proceedings of the National Academy of Science, 103(48): 18284-18289 (2006).
Hellebrand et al, "*Expression of Intercellular Adhesion Molecule 1 by Activated Hepatic Stellate Cells*", Hepatology, 24: 670-676 (1996).
Hurst et al, "*New IL-17 Family Members Promote Th1 or Th2 Responses in the Lung: In Vivo Function of the Novel Cytokine IL-25*", Journal of Immunology, 169: 443-453 (2002).
Ikeda et al, "*Mast cells produce interleukin-25 upon FceRI-mediated activation,*" Blood, 101: 3594-3596 (2003).
Kang, et al., "Interleukin-25 and Interleukin-13 Production by Alveolar Macrophages in Response to Particles," American Journal of Respiratory and Cellular Molecular Biology, 33: 290-296 (2005).
Kim et al, "*Transgenic overexpression of human IL-17E results in eosinophilia, B-lymphocyte hyperplasia and altered antibody production*", Blood, 42: 2330-2342 (2002).
Kishimoto, et al., "Interleukin-6 and Its Receptor: A Paradigm for Cytokines," Science, 258: 593-597 (1992).
Kisselva et al, "*Bone Marrow-derived fibrocytes participate in pathogenesis of liver fibrosis*", Journal of Hepatology, 2006, 45: 429-438 (2006).
Knappik et al, "*Fully Synthetic Human Combinatorial Antibody Libraries (HuCAL) Based on Modular Consensus Frameworks and CDRs Randomized with Trinucleotides*", Journal of Molecular Biology, 296: 57-86 (2000)..
Kohler et al, "*Continuous cultures of fused cells secreting antibody of predefined specificity*" Nature, 256: 495-497 (1975).
Kovacs et al., "*Fibrogenic cytokines and connective tissue production*", FASEB Journal, 8: 854-861 (1994).
Krebs et al, "*High-throughput generation and engineering of recombinant human antibodies*", Journal of Immunological Methods, 254: 67-84 (2001).
Lajoie-Kadoch et al, "*TNF-a and IFN-y inversely modulate expression of the IL-17E receptor in airway smooth muscle cells*", American Journal of Physiology—Lung, Cell and Molecular Physiology, 290: L1238-L1246 (2006).
Lee et al, "*IL-17E, a Novel Proinflammatory Ligand for the IL-17 Receptor Homolog IL-17Rh1*", Journal of Biological Chemistry, 276: 1660-1664 (2001).
Letuve et al., "*IL-17E upregulates the expression of proinflammatory cytokines in lung fibroblasts*", Journal of Allergy and Clinical Immunology, 117: 590-596 (2006).
Libermann and Baltimore, "*Activation of Interleukin-6 Gene Expression through the NF-kB Transcription Factor*", Molecular and Cellular Biology, 10(5): 2327-2334 (1990).
Lonberg et al, "*Antigen-specific human antibodies from mice comprising four distinct genetic modifications*", Letters to Nature, 368:856-859 (1994).
Maezawa et al, *Involvement of TNF Receptor-Associated Factor 6 in IL-25 Receptor Signaling*, Journal of Immunology, 176: 1013-1018 (2006).
Mauviel et al., "*Leukoregulin, a T Cell-derived Cytokine Induces IL-8 Gene Expression and Secretion in Human Skin Fibroblasts*", Journal of Immunology, 149(9): 2969-2976 (1992)..
Mehrad et al, "*Circulating peripheral blood fibrocytes in human fibrotic interstitial lung disease*", Biochemical and Biophysical Research Communication, 353: 104-108 (2007).
Mendez et al, "*Functional transplant of megabase human immunoglobulin loci recapitulates human antibody response in mice*", Nature Genetics, 15: 146-156 (1997).
Moore et al, "*CCR2-Mediated Recruitment of Fibrocytes to the Alveolar Space After Fibrotic Injury*", American Journal of Pathology, 166(3): 675-684 (2005).
Moore et al, "*The role of CCL12 in the Recruitment of Fibrocytes and Lung Fibrosis*", American Journal of Respiratory and Cellular and Molecular Biology, 35: 175-181 (2006).
Murphy et al, "*Regulation of Interleukin 12 p40 Expression through an NF-kB Half-Site,*" Molecular and Cellular Biology, 15(10): 5258-5267 (1995).
Nimphius et al, "*CD34 fibrocytes in chronic cystitis and noninvasive and invasive urothelial carcinomas of the urinary bladder*", Virchows Archives, 450: 179-185 (2007).
Owyang, et al., "Interleukin 25 regulates type 2 cytokine-dependent immunity and limits chronic inflammation in the gastrointestinal tract," Journal of Experimental Medicine, 203(4): 843-849 (2006).
Pan et al, "*Forced Expression of Murine IL-17E Induces Growth Retardation, Jaundice, a Th2-Biased Response, and Multiorgan Inflammation in Mice*", Journal of Immunology, 167: 6559-6567 (2001).
Phillips et al, "*Circulating fibrocytes traffic to the lungs in response to CXCL12 and mediate fibrosis*", Journal of Clinical Investigation, 114(3): 438-446 (2004).
Pilling, et al., "Inhibition of Fibrocyte Differentiation by Serum Amyloid $P^1$," The Journal of Immunology, 171: 5537-5546 (2003).
Quan, et al., "The Role of Circulating Fibrocytes in Fibrosis," Current Rheumatology Reports, 8: 145-150 (2006).
Queen et al, "*A humanized antibody that binds to the interleukin 2 receptor*", Proceedings of the National Academy of Science, 86: 10029-10033 (1989).
Rickel et al, "*Identification of Functional Roles for Both IL-17RB and IL-17RA in Mediating IL-25 Induced Activities*", Journal of Immunology, 181: 4299-4310 (2008).
Ruster et al, "*The Role of chemokines and chemokine receptors in diabetic nephropathy*", Front Bioscience, 13: 944-955 (2008).
Sakai et al., "*Secondary lymphoid tissue chemokine (SLC/CCL21)/CCR7 signaling regulates fibrocytes in renal fibrosis*", Proceedings of the National Academy of Science, 103(38): 14098-14103 (2006).
Schmidt et al, "*Identification of Circulating Fibrocytes as Precursors of Bronchial Myofibroblasts in Asthma*" Journal of Immunology, 171: 380-389 (2003).
Shi et al, "*A Novel Cytokine Receptor-Ligand Pair*", Journal of Biological Chemistry, 275(25): 19167-19176 (2000).
Tacke and Randolph, "Migratory fate and differentiation of blood monocyte subsets", Immunobiology, 211: 609-618 (2006).
Van Deventer et al, "*C-C Chemokine Receptor 5 on Stromal Cells Promotes Pulmonary Metastasis*", Cancer Research, 65(8): 3374-3379 (2005).
Wang, et al., "IL-25 augments type 2 immune responses by enhancing the expansion and functions of TSLP-DC-activated Th2 memory cells," Journal of Experimental Medicine, 204(8): 1837-1847 (2007).
Wong et al, "*Interleukin-25-Induced interleukin-25-Induced Chemokines and Interleukin-6 Release from Eosinophils is Mediated by p38 Mitogen-Activated Protein Kinase, c-Jun N-Terminal Kinase, and Nuclear Factor-kB*", American Journal of Respiratory and Critical Care Medicine, 33: 186-194 (2005).
Yin, et al., "Inhibitory effects of intestinal electric stimulation on food intake, weight loss and gastric emptying in rats," American Journal of Physiology- Regulatory, Integrative and Comparative Physiology, 293: R78-R82 (2006).
PCT International Search Report dated Dec. 15, 2009.
Cheung, et al., "IL-25 regulates the expression of adhesion molecules on eosinophils: mechanism of eosinophilia in allergic inflammation," Allergy, 61: 878-885 (2006).

\* cited by examiner

METHODS FOR MEDIATING FIBROTIC RESPONSE

CROSS-REFERENCE TO RELATED APPLICATIONS

This application claims priority to U.S. Provisional Application Ser. No. 61/110,127, filed 31 Oct. 2008, the entire contents of which is incorporated herein by reference in its entirety.

FIELD OF THE INVENTION

The present invention relates to methods for mediating fibrotic response by modulating IL-25 signaling in fibrocytes and their uses.

BACKGROUND OF THE INVENTION

Inflammation is the coordinated response to tissue injury or infection. Inflammation begins with the local release of chemotactic factors, platelet activation, and initiations of the coagulation and complement pathways. These events stimulate the local endothelium, promoting the extravasation of neutrophils and monocytes. The second phase of inflammation is characterized by the influx into the tissue of cells of the adaptive immune system, including lymphocytes. The subsequent resolution phase, when apoptosis of the excess leukocytes and engulfment by tissue macrophages takes place, is also characterized by repair of tissue damage by stromal cells, such as fibroblasts.

In such repair mechanisms fibroblasts migrate into the affected area and can exhibit an altered phenotype being hyperproliferative or producing excess collagen. Fibroblasts are classically thought of as being predominantly resident cells, however, emerging data has indicated that circulating fibroblast precursor cells, fibrocytes, migrate to the sites of repair or injury, where they differentiate and mediate wound healing, tissue repair and other fibrotic responses, such as pathological fibrosis.

Fibrocytes originate from bone marrow, differentiate from a CD14+ peripheral blood monocyte precursor population and express markers of hematopoietic cells (CD45, MHC class II, CD34), stromal cells (collagen types I and III and fibronectin), as well as chemokine receptors (CCR3, CCR5, CCR7 and CXCR4) (Abe et al., J. Immunol. 166:7556-62, 2001; Moore et al., Am. J. Pathol. 166:675-84, 2005; Bucala et al., Mol. Medicine 1:71-81, 1994). Fibrocytes do not express a variety of endothelial, epithelial or smooth-muscle markers, and are negative for the monocyte/macrophage and dendritic cell specific markers CD4, CD16 and CD25 (Bucala et al., Mol. Med. 1:71-81, 1994; Freudenthal and Steinman PNAS 87:7698-7702, 1990). Thus, an isolated fibrocyte cell is a unique cell type with a defined phenotype readily distinguishable from resident mesenchymal or circulating cells.

Once released from the bone marrow, fibrocyte migration and differentiation into fibroblasts and myofibroblasts is induced by various mediators. CCR2/CCL2, CXCR4/CXCL12, CCR7/CCL21 receptor/ligand pairs have been implicated in the recruitment and accumulation of fibrocytes into tissues during fibrotic processes (Phillips et al., J. Clin. Invest. 114:438-46, 2004; Sakai et al., PNAS 103:14098-103, 2006; Tacke and Randolph, Immunobiology 211:609-18, 2006). TGF-β1, ET-1, PDGF, IL-4 and IL-13 have been shown to promote fibrocyte differentiation into mature fibroblasts and myofibroblasts with acquirement of increased production of collagen and other ECM proteins, downregulation of CD34 and CD45, and expression of the myofibroblast marker α-smooth muscle actin (α-SMA). The in vivo differentiation of fibrocytes from circulating precursors may mainly occur at the tissue site and not in the peripheral blood (Haudek et al., PNAS 103:18284-289, 2006; Frid et al., Am. J. Pathol. 168:659-69, 2006). In addition to production of ECM proteins, fibrocytes secrete inflammatory cytokines (TNF-α and TGF-β), hematopoietic growth factors (IL-6, IL-10, M-CSF), growth factors (TGF-α, VEGF, PDGF-A, HGF, CNTGF, bFGF) and chemokines (CCL2, CCL3, CCL4, CXCL1, CXCL8) (Abe et al., J. Immunol. 166:7556-62, 2001; Chesney et al., J. Immunol. 160:419-25, 2006; Chesney et al., Curr. Rheumatol. Rep. 2:501-5, 2000).

Mature fibrocytes rapidly enter sites of tissue injury where they secrete inflammatory cytokines, extracellular matrix proteins, other cytokines and pro-angiogenic molecules, playing a role in a number of human diseases. Human and mouse studies have demonstrated that fibrocytes from peripheral blood migrate to skin wound chambers (Bucala et al., Mol. Med. 1:71-81, 1994; Chesney et al. J. Immunol. 160: 419-25, 1998; Abe et al., J. Immunol. 166:7556-62, 2001) and bronchial mucosa after antigen challenge. Fibrocytes have been reported in disease states with fibrotic pathologies including asthma and idiopathic pulmonary fibrosis (Schmidt et al. J. Immunol. 171:380-89, 2003; Abe et al., Am. J. Prespir. Crit. Care Med. 170:1158-63, 2004; Moore et al. Am. J. Pathol. 166:675-84, 2005), and excessive myofibroblast proliferation is associated with Crohn's disease (Am. J. Physiol. Gastrointest. Liver Physiol. 295:G581-90, 2008). In murine models, fibrocytes have been shown to contribute to the pathogenesis of pulmonary fibrosis and liver fibrosis, in the liver fibrocytes contributing to collagen deposition (Kisselva et al., J. hepatology 45:429-38, 2006; Gomperts and Stierter, J. leukocyte Biol. 82:449-56, 2007). There is evidence for a role for fibrocytes in hypertrophic scars or keloids, burns, scleroderma and related disorders. Fibrocytes may contribute to fibrogenesis in several ways as these cells produce collagen and have been shown to differentiate into a more resident myofibroblast phenotype, which may exacerbate the fibrotic environment even further (Moore et al., Am. J. Pathol. 166: 675-84, 2005; Mehrad et al., Biochem. Biophys. Res. Commun. 353:104-8, 2007; Phillips et al., J. Clin. Invest. 114:438-46, 2004; Epperly et al., Am. J. Respir. Cell. Mol. Biol. 29:213-24, 2003; Hashimoto et al., J. Clin. Invest. 113:243-52, 2004; Moore et al., Am. J. Respir. Cell. Mol. Biol. 35:175-81, 2006). Fibrocytes also constitute part of the stromal response to tumor invasion, and these cells may be a prognosticator of malignancy potential (Barth et al., J. Exp. Med. 11:11, 2002; Chauhan et al., J. Clin. Pathol. 56:271-76, 2003). Fibrocyte differentiation into myofibroblasts is also associated with stromal remodeling during invasive carcinomas in the urinary bladder (Nimphius et al., Virchows Arch. 450: 179-85, 2007).

The signals that modulate fibrocyte proliferation and differentiation, cytokine and chemokine secretion, and migration are only partially defined. A better understanding of these signals may enable new therapies to prevent human diseases or conditions with altered fibrocyte function, for example pathologic fibrosis. Thus, there is a need to identify and modulate receptor/ligand interactions that mediate fibrocyte functions.

SUMMARY OF THE INVENTION

One aspect of the invention is a method of suppressing undesired activity in a fibrocyte comprising inhibiting IL-25 signaling in the fibrocyte.

Another aspect of the invention is a method of suppressing undesired activity in the fibrocyte in a subject having a condition associated with undesired activity in the fibrocyte comprising administering to the subject a therapeutically effective amount of an inhibitor of IL-25 signaling.

Another aspect of the invention is a method of identifying modulators of IL-25 signaling that suppress undesired activity in a fibrocyte.

BRIEF DESCRIPTION OF THE FIGURES

FIG. 2. Increased fibrocyte proliferation in response to A) IL-25 in murine lung fibrocytes and B) IL-25 in human blood fibrocytes, and inhibition of proliferation by an IL-25 antagonist C) anti-IL-25 antibody (IL-25 Ab) in murine lung fibrocytes and D) soluble IL-25 receptor (IL-25R) in murine lung fibrocytes.

FIG. 3. A) and B) Increased fibrocyte differentiation in response to IL-25 in A) murine lung and B) human blood fibrocytes and C) inhibition of fibrocyte differentiation by an IL-25 antagonist anti-IL-25 antibody (IL-25 Ab).

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise. Thus, for example, reference to "a polypeptide" is a reference to one or more polypeptides and includes equivalents thereof known to those skilled in the art.

Unless defined otherwise, all technical and scientific terms used herein have the same meaning as commonly understood by one of ordinary skill in the art to which an invention belongs. Although any compositions and methods similar or equivalent to those described herein can be used in the practice or testing of the invention, exemplary compositions and methods are described herein.

As used herein, the term "suppress" or "suppressing" means partially or totally blocking stimulation, decreasing, preventing, delaying activation, inactivating, desensitizing, inhibiting, or down regulating a measurable change in cell function, for example change in IL-25 signaling or change in an undesired activity in a fibrocyte. Suppressing a measurable change in cell function is achieved when the activity value assigned to the cell function relative to the control is 50-80%, optionally 25-50% or 0-25%, where control samples are assigned a relative activity value of 100%. Suppressing a measurable change in cell function can be achieved by various strategies. For example, suppressing IL-25 signaling can be achieved by blocking IL-25 and IL-25 receptor interaction or suppressing IL-25 receptor expression.

"Undesired activity in a fibrocyte" as used herein means an undesired measurable function by a fibrocyte, for example collagen secretion by the fibrocyte, protein secretion by the fibrocyte, fibrocyte differentiation, fibrocyte proliferation, or fibrocyte migration. Fibrocytes are mesenchymal progenitor cells that demonstrate morphological and molecular characteristics of monocytes, fibroblasts and hematopoietic cells. Fibrocytes can be circulating or tissue resident, for example pulmonary, liver, or kidney resident fibrocytes. Surface expression of CD45 and collagen production is considered a sufficient criterion to discriminate fibrocytes both in vivo and in vitro from other circulating or tissue-resident mesenchymal cells (Bellini and Mattoli, Lab. Investig. 87:858-870, 2007).

"Fibrocyte proliferation" as used herein means the ability of the fibrocyte to divide, for example upon PDGF stimulus.

"Fibrocyte differentiation" as used herein means the ability of the fibrocyte to differentiate into a myofibroblast or fibroblast. Differentiation of fibrocytes into myofibroblasts can be induced for example by TGF-β1 and endothelin-1 (ET-1), and the differentiation assessed by evaluating expression of myfibroblast differentiation markers for example α-smooth muscle actin (α-SMA).

"Protein secretion by the fibrocyte" as used herein means induced or steady state secretion of proteins and peptides by fibrocytes, for example cytokines such as IL-4, IL-5, IL-13, TNF-α and TGF-β, hematopoietic growth factors such as IL-6, IL-10 and M-CSF, growth factors such as TGF-α, VEGF, PDGF-A, HGF, CNTGF, bFGF, and chemokines such as CCL2, CCL3, CCL4, CXCL1, CXCL8, MIP-1α, MIP-1β, MCP-1, IL-8 and GROα (Chesney et al. 1998; Chesney and Bucala 2000; Abe et al. 2001).

The term "IL-25 receptor" as used herein means a receptor or a receptor complex mediating IL-25 signaling. IL-25 signaling requires two receptors, IL17RB and IL17RA, which may form a heteromeric complex. IL-25 binds to IL17RB with high affinity, whereas IL17RA does not bind IL-25 but is required for activating signaling pathways upon ligand binding (Rickel et al., J. Immunology 181:4299-310, 2008). Thus, "IL-25 receptor" contemplates both IL17RB and IL17RA. The term "IL17RB" (IL-17BR, CRL4, EVI27, IL17RH1, or MGC5245) as used herein means "interleukin 17 receptor B", a polypeptide having an amino acid sequence according to GenBank Acc. No. NP_061195, the product of the human IL17RB receptor gene, and include all of the variants, isoforms and species homologs of IL17RB. Both IL-25 and IL-17B are ligands for IL17RB, but the receptor binds IL-25 with higher affinity (Lee, et al., J. Biol. Chem. 276, 1660-64, 2001). The term "IL17RA", (CD217, IL17R, CDw217, IL-17RA, hIL-17R, or MGC10262) as used herein means "interleukin 17 receptor A", a polypeptide having an amino acid sequence according to GenBank Acc. No. NP_055154, the product of the human IL17RA receptor gene, and include all of the variants, isoforms and species homologs of IL17RA. Variants of IL17RB and IL17RA also include soluble mature receptors.

The term "IL-25" or "IL-25 polypeptide" (IL17E, or IL-17E) as used herein means "interleukin-25", a polypeptide having a sequence according to GenBank Acc. No. NP_073626 or NP_758525, the product of the human IL-25 gene, and include all of the variants, isoforms or species homologs of IL-25.

"IL-25 signaling" as used herein means the processes initiated by IL-25 or a second IL-25 receptor ligand interacting with the IL-25 receptor on the cell surface, resulting in measurable changes in cell function. IL-25 receptor complex includes I17RB and IL17RA, and ligand binding activates downstream signal transduction pathways for example adaptor molecule TRAF6, JNK/p38 and ERK, and NF-κB, leading to the production of cytokines and chemokines (Maezawa et al, J. Immunol. 176:1013-18, 2006). IL-25 signaling can be measured for example by assessing the amount of cytokines and chemokines produced upon induction with an IL-25 receptor ligand, for example measuring production of CXCL-8, IL-6, G-CSF, MCP-1, MIP-1α, RANTES, or CCL2 (Cai et al., Cytokine 16:10-21, 2001; Lee et al., J. Biol. Chem. 276: 1660-64, 2001; Pan et al., J. Immunol. 167:6559-67, 2001; Wong et al., Am. J. Respir. Cell. Mol. Biol. 33:186-194, 2005). IL-25 signaling can also be assessed by functional assays measuring for example effect of IL-25 receptor ligand on cell proliferation or differentiation, or using reporter genes and reporter gene constructs operatively linked to a promoter sensitive to NF-κB. Examples of such promoters include those for IL-6, IL-8 and IL-12 p40 (Murphy et al., Mol. Cell. Biol. 15:5258-67, 1995; Libermann and Baltimore, Mol. Cell. Biol. 10:2327-34, 1990; Mauviel et al., J. Immunol. 149:2969-76, 1992). Activation of intracellular kinases for example JNK/p38 can be measured by phoshpo-antibodies, and assaying secreted molecules or measuring cell proliferation or differentiation can be done using enzyme-linked immunosorbent assay (ELISA) or a spectrum of bioassays. The methods and suitable readout systems are well known in the art and are commercially available. For example, IL-25 signaling in fibrocytes can be measured by stimulating the fibrocytes with IL-25 alone or together with a second stimulus, for example TNF-α, and measuring the amount of secreted IL-6 and RANTES in the culture media in comparison to a control fibrocyte culture that was not stimulated with IL-25.

The term "ligand" refers to a peptide or polypeptide, a small molecule, or an oligonucleotide that binds to, or complexes with the IL-25 receptor or variant thereof. The ligand may be an antagonist, inhibitor, suppressor, agonist, stimulator or activator, or the like, of IL-25 receptor. Exemplary ligands are IL-25 and IL-17F.

The term "agent" as used herein refers to polypeptides, peptides or proteins, fusion proteins, peptidomimetics, antibodies, antibody fragments, nucleic acids, oligonucleotides, synthetic oligonucleotides, small molecules and the like that inhibit IL-25 signaling. The agent can be identified using assays measuring IL-25 signaling, which are described above. Examples of agents include a soluble mature IL17RB, IL-25 polypeptide, IL-25 antibody, antagonistic IL-25 receptor antibody, or antagonist IL17RB antibody.

The term "modulator" as used herein means a molecule or preparation that is believed to provide a therapeutic benefit in humans or other animals and is believed to provide that therapeutic benefit, in part, through activating or suppressing IL-25 signaling in fibrocytes. The term "modulator" includes inhibitors and activators. "Inhibitors" are agents that partially or totally block stimulation, decrease, prevent, delay activation, inactivate, desensitize or down regulate a measurable process in a cell, for example IL-25 signaling, e.g., antagonists or antagonistic. Activators are agents that stimulate, increase, open, activate, facilitate, enhance activation, sensitize, or up regulate a measurable process in a cell, for example IL-25 signaling, e.g., agonists. For example, modulator of IL-25 signaling can interact directly with IL-25 or components of the IL-25 receptor, usually binding to IL-25 receptor, any component of the IL-25 receptor, or IL-25 receptor ligand with an affinity constant of about $10^{-6}$ M, about $10^{-8}$ M, about $10^{-9}$ M, or about $10^{-10}$ M. The modulator can also modulate IL-25 signaling indirectly, for example modulating IL-25 receptor expression. Modulators include antibodies, antibody fragments, peptides, polypeptides, oligonucleotides, small chemical molecules and the like.

"Test modulator" as used herein means a modulator that is under evaluation for the ability to activate or suppress the measurable process in a cell, for example undesired activity in the fibrocyte by modulating IL-25 signaling.

The term "antibody" as used herein refers to a molecule specifically binding to an antigen, and includes dimeric, trimeric and multimeric antibodies, and chimeric, humanized and fully human antibodies. An antibody may be a whole antibody or a functional fragment of an antibody molecule, such as a fragment retaining at least its antigen binding function, and include Fab, F(ab'), F(ab')$_2$, scFv, dsFv, and diabodies. For example, antibody fragments may be obtained using proteolytic enzymes (e.g., a whole antibody is digested with papain to produce Fab fragments, and pepsin treatment results in the production of F(ab')$_2$ fragments). Techniques for the preparation and use of the various antibodies are well known in the art (Ausubel, et al., ed., Current Protocols in Molecular Biology, John Wiley & Sons, Inc., NY 1987-2001; Sambrook, et al., Molecular Cloning: A Laboratory Manual, 2$^{nd}$ Edition, Cold Spring Harbor, N.Y., 1989; Harlow and Lane, Antibodies, a Laboratory Manual, Cold Spring Harbor, N.Y., 1989; Colligan, et al., ed., Current Protocols in Immunology, John Wiley & Sons, Inc., NY 1994-2001; Colligan et al., Current Protocols in Protein Science, John Wiley & Sons, NY, N.Y., 1997-2001; Kohler et al., Nature 256:495-497, 1975; U.S. Pat. No. 4,816,567, Queen et al., Proc. Natl. Acad. Sci. 86:10029-10033, 1989). For example, fully human monoclonal antibodies lacking any non-human sequences can be prepared from human immunoglobulin transgenic mice or from phage display libraries (Lonberg et al., Nature 368:856-859, 1994; Fishwild et al., Nature Biotech. 14:845-851, 1996; Mendez et al., Nature Genetics 15:146-156, 1997; Knappik et al., J. Mol. Biol. 296:57-86, 2000; Krebs et al., J. Immunol. Meth. 265:67-84, 2001).

An agent, a modulator, an antibody molecule or the like "specifically binds" a given antigen or protein when it binds this antigen or protein with higher affinity and in a specific, as opposed to non-specific fashion, relative to a second non-identical antigen or protein. Stated differently, the "specific binding" of an agent, a modulator, an antibody molecule or the like can be used to distinguish between two different polypeptides.

A "fragment" is a polypeptide having an amino acid sequence that comprises a portion, but not all, of any amino acid sequence of any polypeptide of the invention. Fragments can include, for example, truncated polypeptide having a portion of an amino acid sequence corresponding to a signal peptide, extracellular domain, transmembrane domain, or cytoplasmic domain, or variants thereof, such as a continuous series of residues that includes a heterologous amino- and/or carboxy-terminal amino acid sequence. Degradation forms of the polypeptides of the invention produced by, or in, a host cell are also included. Other exemplary fragments are characterized by structural or functional attributes such as fragments that comprise alpha-helix or alpha-helix forming regions, beta-sheet or beta-sheet forming regions, turn or turn-forming regions, coil or coil-forming regions, hydrophilic regions, hydrophobic regions, alpha-amphipathic regions, beta-amphipathic regions, flexible regions, surface-forming regions, substrate binding regions, extracellular regions and high antigenic index regions. The polypeptides of the invention can be used or provided as fragments.

The term "polypeptide" means a molecule that comprises at least two amino acid residues linked by a peptide bond to form a polypeptide. Small proteins of less than 30 amino acids may be referred to as "peptides". Polypeptides may also be referred as "proteins".

The present invention relates to methods of suppressing undesired activity in a fibrocyte by inhibiting IL-25 signaling. The invention is based on a discovery that IL-25 receptor is present in the fibrocytes, and inhibition or activation of IL-25 signaling modulates various activities in the fibrocytes, for example fibrocyte proliferation, differentiation, and protein secretion; IL-25 thus acting as a pro-inflammatory, pro-proliferative and differentiation factor for this cell type. Fibrocytes migrate to the site of tissue injury where they secrete extracellular matrix proteins, inflammatory cytokines, extracellular matrix proteins, other cytokines and pro-angiogenic molecules, playing a role in various human diseases, including fibrotic conditions. Thus, inhibition of IL-25 signaling in the fibrocyte may be useful for the treatment of conditions associated with undesired activity in the fibrocytes, for example fibrotic conditions.

In one embodiment, the invention provides a method of suppressing undesired activity in a fibrocyte comprising inhibiting IL-25 signaling in the fibrocyte. IL-25 (also known as IL-17E), a member of the IL-17 family, is implicated in Th2 cell-mediated immunity (Fort et al., Immunity 15:985-995 2001; Hurst et al., J. Immunol. 169:443-453. 2002). Animal models of IL-25 or IL-25 administration to animals demonstrate IL-25-induces Th2-like responses associated with multiorgan inflammation, inflammatory cell infiltration, and epithelial cell hyperplasia, driven by IL-25 induced expression of IL-4, IL-5, and IL-13 (Shi et al., J. Biol. Chem. 275:19167-76, 2000; Lee et al., J. Biol. Chem. 276:1660-64, 2001; Hurst et al., 2002; J. Immunol. 169:443-53, 2002; Kim et al., Blood 100:2330-42, 2002). The molecular mechanisms whereby IL-25 regulates type 2 immunity are still unclear. A non-B/T cell population was found to be regulated by IL-25 and produce Th2 cytokines in response to *Nippostrongylus brasiliensis* infection (Fallon et al., J. Exp. Med. 203:1105-1116, 2006). However, given the broad expression of IL17RB, additional targets of IL-25 may exist to regulate IL-25 responses. In vitro, IL-25 is found to be expressed in activated Th2 cells and bone marrow-derived mast cells (Fort et al., Immunity 15:985-995 2001; Ikeda et al., Blood 101: 3594-96, 2003). Activated eosinophils and basophils from normal and atopic subjects have been found to secrete bioactive IL-25 protein (Wang et al., J. Exp. Med. 204:1837-47, 2007). IL-25 is also upregulated in alveolar macrophages in a model of particle induced airway inflammation in rats and in mouse (MLE12 cell line) and human (A549) lung epithelial cells after allergen stimulation (Fort et al., Immunity 15:985-995 2001; Ikeda et al., Blood 101:3594-96, 2003). Target cells for IL-25 that have been identified include alternatively activated macrophages, dendritic cells, lung fibroblasts, airway smooth muscle cells, naïve T and TH2 cells, which express IL17RB in vitro (Gratchev et al., J. Immunol. 60:233-37, 2004; Lajoie-Kadoch et al., Am. J. Physiol. Lung cell Mol. Physiol. 290:L1238-46, 2006; Letuve et al., J. Allergy Clin. Immunol. 117:590-96, 2006; Angkasekwinai et al., J. Exp. Med. 11:11, 2007).

IL-25 signaling in a fibrocyte can be inhibited using various agents and inhibitors of IL-25 signaling. The agents and inhibitors can target IL-25 and/or IL-25 receptor, or specifically inhibit the interaction of IL-25 with the IL-25 receptor. Such agents and inhibitors are for example antibodies or antibody fragments against IL-25 or IL-25 receptor, recognizing extracellular portions of the receptor polypeptides, antisense or siRNA molecules designed against IL-25 or IL-25 receptor genes, or soluble IL-25 receptors comprising soluble IL17RB or soluble IL17RA receptor polypeptides. Peptides, oligonucleotides or small molecules blocking interaction between IL-25 and the IL-25 receptor can be used. Such agents and inhibitors can also be peptides, proteins, fusion proteins, or small molecules that prevent interaction of IL-25 with the IL-25 receptor. Agents inhibiting IL-25 have been described (U.S. Pat. No. 6,562,578 to Gorman; U.S. Pat. No. 6,635,443 to Shi). IL-25 signaling in a fibrocyte and undesired activity in a fibrocyte can be measured using various methods as described above.

It is possible to modify the structure of the polypeptides or fragments used as agents to inhibit IL-25 signaling in a fibrocyte for such purposes as enhancing substrate specificity, stability, solubility, and the like. For example, a modified polypeptide can be produced in which the amino acid sequence has been altered, such as by amino acid substitution, deletion, or addition. It is contemplated that an isolated replacement of a leucine with an isoleucine or valine, an aspartate with a glutamate, a threonine with a serine, or a similar replacement of an amino acid with a structurally related amino acid (i.e., conservative mutations) will, in some instances but not all, not have a major effect on the biological activity of the resulting molecule. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally being grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed., WH Freeman and Co., 1981). Whether a change in the amino acid sequence of a polypeptide or fragment thereof results in a functional homolog can be readily determined by assessing the ability of the modified polypeptide or fragment to produce a response in a fashion similar to the unmodified polypeptide or fragment using the assays described herein. Peptides, polypeptides or proteins in which more than one replacement has taken place can readily be tested in the same manner.

The agent inhibiting IL-25 signaling in a fibrocyte can be conjugated to a second polypeptide to form a fusion protein that can confer desirable properties, for example increased stability. Exemplary fusion proteins can be formed by conjugating together a soluble mature IL17RB and an alternative scaffold such as designed ankyrin repeat protein (DARPins) (Stumpp and Amstutz, Curr. Opin. Durg Discov. Devel. 10:153-159, 2007), MIMETIBODY™ construct (Picha et al., Diabetes 57:1926-1934, 2008), or other protein domains. Proteins, peptides or fusion proteins may generally be generated using either recombinant nucleic acid methods or by chemical synthesis methods well known in the art. A MIMETIBODY™ construct has the generic formula (I):

$$(Bp\text{-}Lk\text{-}V2\text{-}Hg\text{—}C_H2\text{-}C_H3)_{(t)}, \qquad (I)$$

where Bp is a peptide or polypeptide capable of binding a molecule of interest, Lk is a polypeptide or chemical linkage, V2 is a portion of a C-terminus of an immunoglobulin variable region, Hg is at least a portion of an immunoglobulin variable hinge region, $C_H2$ is an immunoglobulin heavy chain $C_H2$ constant region and $C_H3$ is an immunoglobulin heavy chain $C_H3$ constant region, and t is independently an integer of 1 to 10.

While not wishing to bound to any theory, it is thought that the method of inhibiting IL-25 signaling in a fibrocyte inhibits fibrocyte differentiation, proliferation or cytokine and chemokine secretion in a tissue, reducing amounts of collagen, extracellular matrix proteins and pro-inflammatory cytokines fibrocytes produce at a site of injury, inflammation, or fibrotic area.

Another embodiment of the invention is a method of suppressing undesired activity in a fibrocyte in a subject having a condition associated with undesired activity in the fibrocyte comprising administering to the subject a therapeutically effective amount of an inhibitor of IL-25 signaling.

"Subject" refers to any animal, preferably a human patient, livestock, or domestic pet. Without wishing to be bound by any particular theory, it is believed that the therapeutic benefit of the methods of the invention will be due to the inhibition of IL-25 signaling resulting in reduced collagen and proinflammatory cytokine secretion at a site of injury, repair, or in pathological conditions such as fibrosis.

"A condition associated with undesired activity in the fibrocyte" as used herein include conditions that are associated with abnormal activity in either tissue or circulating fibrocytes, for example conditions associated with increased collagen secretion or increased fibrocyte differentiation into the myofibroblast. Examples of such conditions are fibrotic conditions, cancer, and wound healing.

The fibrotic condition can be organ specific fibrosis or systemic fibrosis. The organ specific fibrosis can be lung fibrosis, liver fibrosis, kidney fibrosis, heart fibrosis, pancreatic fibrosis, vascular fibrosis, skin fibrosis, eye fibrosis, or bone marrow fibrosis. The lung fibrosis can be associated with idiopathic pulmonary fibrosis, drug induced pulmonary fibrosis, asthma, sarcoidosis, interstitial idiopathic pneumonia, or chronic obstructive pulmonary disease. The liver fibrosis can be associated with cirrhosis, schistomasomiasis or cholangitis. The cirrhosis can be selected from post-hepatitis C cirrhosis, post-hepatitis B cirrhosis, alcohol, drug, or chemically induced cirrhosis, or primary biliary cirrhosis. The cholangitis can be sclerosing cholangitis. The kidney fibrosis can be associated with diabetic nephropathy, lupus glomeruloschelerosis, proliferative glomerulonephritis, sclerosing glomerulonephritis, or nephrogenic fibrosing dermapathy. The heart fibrosis can be associated with myocardial infarction, coronary artery restenosis, congestive cardiomyopathy, or heart failure. The pancreatic fibrosis can be associated with stromal remodeling, pancreatitis or stromal fibrosis. The vascular fibrosis can be associated with postangioplasty arterial restenosis, or atherosclerosis. The skin fibrosis can be associated with burn scarring, hypertrophic scarring, keloid, scleroderma, psoriasis, or nephrogenic fibrosing dermatopathy. The eye fibrosis can be associated with retro-orbital fibrosis, postcataract surgery, proliferative vitreoretinopathy, corenal fibrosis, corneal scarring due to surgery, or anterior capsule cataract. The bone marrow fibrosis can be associated with idiopathic myelofibrosis or drug induced myelofibrosis. Other fibrotic conditions can be associated with Peyronie's disease, Dupuytren's contracture, Crohn's disease, dermatomyositis, rheumatoid arthritis, fibrotic lesions such as those formed after Schistosoma japonicum infection, autoimmune diseases, pathogenic fibrosis, Lyme disease, chronic cystitis, uterine fibroids, ovarian fibrosis, other fibrocystic formations, wide angle glaucoma trabeculotomy, or fibrotic adhesions resulting from surgical procedures. The systemic fibrosis can be associated with systemic sclerosis, nephrogenic systemic fibrosis, or graft versus host disease.

For example, in asthma, fibrocytes further differentiate into myofibroblasts, which persist in thickened airway walls. While not wishing to bound to any theory, it is thought that inhibition of IL-25 signaling in the fibrocyte may suppress fibrocyte differentiation into the myofibroblast, thus ameliorating symptoms of asthma.

For example in liver cirrhosis, fibrocytes can migrate to the liver and contribute to collagen secretion and fibrosis (Kisselva et al., J. Hepatology, 45:429-438, 2000). While not wishing to be bound to any theory, it is thought that inhibition of IL-25 signaling in the fibrocyte may suppress fibrocyte collagen production in the liver, thus preventing or delaying fibrosis due to liver cirrohsis.

Exemplary cancers may include leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignant lymphoma, non-Hodgkin's lymphoma, Burkitt's lymphoma, multiple myeloma, Kaposi's sarcoma, colorectal carcinoma, pancreatic carcinoma, renal cell carcinoma, breast cancer, skin cancer, cervical cancer, pancreatic cancer, nasopharyngeal carcinoma, malignant histiocytosis, paraneoplastic syndrome/hypercalcemia of malignancy, solid tumors, adenocarcinomas, squamous cell carcinomas, sarcomas, malignant melanoma, particularly metastatic melanoma, hemangioma, metastatic disease, cancer related bone resorption, cancer related bone pain, and the like.

Exemplary wound healing can be associated with trauma or tissue injury or chronic conditions resulting from or related thereto, in a cell, tissue, organ, animal or patient, for example bodily injury or a trauma associated with surgery including thoracic, abdominal, cranial, or oral surgery; or wherein the wound can be selected from the group consisting of aseptic wounds, contused wounds, incised wounds, lacerated wounds, non-penetrating wounds, open wounds, penetrating wounds, perforating wounds, puncture wounds, septic wounds, infarctions and subcutaneous wounds; or wherein the wound can be selected from the group consisting of ischemic ulcers, pressure sores, fistulae, severe bites, thermal burns and donor site wounds; or wherein the wound is an aphthous wound, a traumatic wound or a herpes associated wound. Donor site wounds are wounds which e.g. occur in connection with removal of hard tissue from one part of the body to another part of the body e.g. in connection with transplantation. The wounds resulting from such operations are very painful and an improved healing is therefore most valuable. Wound fibrosis is amenable to suppression of undesired activity by a fibrocyte by inhibiting IL-25 signaling, as fibrocytes migrate to the wound area and start producing collagen as well as proangiongenic factors. Almost all tissue repair processes include the early connective tissue formation, a stimulation of this and the subsequent processes improve tissue healing, however, overproduction of connective tissue and collagen can lead to a fibrotic tissue characterized as inelastic and hypoxic. Suppression of collagen production by the fibrocytes by inhibiting IL-25 signaling in a subject can be useful for modulating, treating or preventing such sequelae of wound healing.

By methods of suppressing undesired activity in the fibrocyte in a subject it should be understood that any suppression of the undesired activity by the fibrocyte is a beneficial effect and can result in the ameliorating of symptoms in a subject having a condition associated with the undesired activity in the fibrocyte. Thus, methods of the invention can result in preventing appearance of a clinical symptom, inhibiting, arresting or delaying the condition, or relieving or causing regression of the condition.

Inhibitors of IL-25 signaling are described above, and can be for example IL-25 antibody, IL-25 receptor antibody or soluble mature IL-25 receptor polypeptide. Amounts of a given inhibitor sufficient to suppress undesired activity in the fibrocyte in a subject can be readily determined. In the methods of the invention, the inhibitor may be administered singly or in combination with a second inhibitor. Such second inhibitor may be an antibody, antibody fragment, peptide, polypeptide, oligonucleotide, or small molecule inhibiting IL-25 signaling. "In combination with" as used herein means that the described inhibitor can be administered to a subject together in a mixture, concurrently as single inhibitor or sequentially as single inhibitors in any order.

The "therapeutically effective amount" of the inhibitor of IL-25 signaling for suppressing undesired activity in the fibrocyte in a subject having a condition associated with undesired activity in the fibrocyte can be determined by standard research techniques. For example, the dosage of the inhibitor which will be effective in suppressing undesired activity in the fibrocyte in conditions such as pulmonary fibrosis or liver fibrosis can be determined by administering the inhibitor to an animal model of pulmonary fibrosis or liver fibrosis.

An exemplary model for pulmonary fibrosis is generated by injection of bleomycin into their lungs. Bleomycin is an antineoplastic agent that, when injected into the airway, causes fibrosis in the lungs of an animal, and is a standard way to study lung fibrosis (Crouch, Am. J. Physiol. Lung Cell Mol. Physiol. 259:L159-L184). An exemplary model for liver fibrosis is generated by ligation of the common bile duct, and is a standard way to study liver fibrosis (Hellebrand C et al., Hepatology 24:670-76, 1996).

In addition, in vitro assays can optionally be employed to help identify optimal dosage ranges. Selection of a particular effective dose can be determined (e.g., via clinical trials) by a skilled artisan based upon the consideration of several factors. Such factors include the disease to be treated or prevented, the symptoms involved, the patient's body mass, the patient's immune status and other factors known by the skilled artisan. The precise dose to be employed in the formulation will also depend on the route of administration, and the seriousness of the disease-related wasting, and should be decided according to the judgment of the practitioner and each patient's circumstances. Effective doses can be extrapolated from dose-response curves derived from in vitro or animal model test systems. The dose of the inhibitor to be administered to a patient, such as a human, is rather widely variable and can be subject to independent judgment. It is often practical to administer the daily dose of the inhibitor at various hours of the day. However, in any given case, the amount of the inhibitor administered will depend on such factors as the solubility of the inhibitor, the formulation used, patient condition (such as weight), and/or the route of administration.

The mode of administration for suppressing undesired activity in a fibrocyte of an inhibitor of IL-25 signaling may be any suitable route that delivers the agent to the host. The proteins, protein fragments, fusion proteins, antibodies and antibody fragments and pharmaceutical compositions of these inhibitors are particularly useful for parenteral administration, e.g., intradermal, intramuscular, intraperitoneal, intravenous, subcutaneous or intranasal.

The inhibitors of IL-25 signaling can be prepared as pharmaceutical compositions containing an effective amount of the agent as an active ingredient in a pharmaceutically acceptable carrier. The term "carrier" refers to a diluent, adjuvant, excipient, or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the agent of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected. Actual methods for preparing parenterally administrable compositions are well known and are described in more detail in, for example, "Remington's Pharmaceutical Science", $15^{th}$ ed., Mack publishing Company, Easton, Pa.

Another aspect of the invention is a method of identifying modulators of IL-25 signaling that suppress the undesired activity in the fibrocyte, by providing fibrocytes; providing a test modulator; contacting the fibrocytes with the test modulator; determining an effect of the test modulator on IL-25 signaling; determining the effect of the test modulator on the undesired activity in the fibrocyte; and selecting the modulator that modulates IL-25 signaling; and modulates the undesired activity in the fibrocyte. These modulators may be natural or synthetic, inhibitors or activators of IL-25 signaling, and can be identified using one or more assays evaluating IL-25 signaling and activity in a fibrocyte as described above.

Fibrocytes can be isolated from peripheral blood or tissue, purified and cultured as adherent cultures using standard methods (Bucala et al., Mol. Medicine 1:71-81, 1994). For example, PBMC are isolated by centrifugation over Ficoll-Paque, and cultured in adherent culture. Non-adherent cells are removed, and fibrocytes are further purified from contaminating T-cells, B-cells and monocytes by negative immunoselection with anti-CD2, anti-CD19, and anti-CD14 antibodies, respectively. Expression of CD45, CD34 and collagen I in the purified population confirms the fibrocyte origin (Bellini and Mattoli, Lab. Investigation 87:858-70, 2007).

The test modulator is incubated with IL-25 responsive fibrocytes, and the effect of the modulator in both IL-25 signaling and activity in a fibrocyte is evaluated. The test modulator can directly bind IL-25 or IL-25 receptor, or indirectly modulate IL-25 signaling in the fibrocyte. The test modulator can be screened in a substantially purified form or in a crude mixture. The test modulators can be antibodies, antibody fragments, proteins, peptides, small molecules, or oligonucleotides.

In an exemplary screening assay, cultured fibrocytes are contacted with IL-25 and a test modulator, and effect of the test modulator on IL-25-induced cytokine secretion and fibrocyte differentiation is measured. Cytokines measured are for example IL-6 and RANTES, and fibrocyte differentiation can be measured by assessing amount of $\alpha$-SMA in the fibrocyte. Methods of detecting cytokine secretion and assessing fibrocyte differentiation are well known and described above.

The present invention now being fully described, it will be apparent to one of ordinary skills in the art that many changes and modifications can be made thereto without departing from the spirit or scope of the appended claims. The specific embodiments described herein are offered by way of example only, and the invention is to be limited by the terms of the appended claims, along with the full scope of equivalents to which such claims are entitled, and the invention is not to be limited by the specific embodiments that have been presented herein by way of example.

Example 1

IL17RB Expression in Human and Rodent Fibrocytes

Fibrocytes have been described to be one of the sources of increased myofibroblasts along with EMT derived fibroblasts and resident fibroblasts that are a hallmark of fibrotic pathologies. Fibrocytes derived from the bone-marrow which have to migrate to sites of tissue injury may enhance fibrosis due to the production of pro-fibrotic and pro-inflammatory factors. Disturbing fibrocyte differentiation, proliferation, or migration could provide a distinct therapeutic path to treat a range of fibrotic diseases.

Murine lung and blood, and human blood fibrocytes were isolated and cultured according to materials and methods. The isolated cells showed irregular star or spindle shape morphology with branching extensions, characteristics of the cell type. Immunocytochemistry showed that murine lung and blood fibrocytes co-stained positive for CD45 and collagen I, markers for fibrocytes (data not shown). Positive IL17RB expression was demonstrated using confocal microscopy in all fibrocyte classes tested, including murine lung and blood fibrocytes (data not shown).

To quantify fibrocyte expression of IL17RB, cells were triple stained with CD45, collagen I and IL17RB and enumerated by flow cytometry. 80% of murine lung fibrocytes and 49% of murine blood fibrocytes were CD45 and collagen I positive. From this population of cells, 40% of lung and 99% of blood fibrocytes were IL17RB positive. Collagen I$^+$ CD45$^-$ (fibroblasts) murine lung cells also expressed IL17RB. Human blood fibrocytes were also evaluated for IL17RB expression, 88% of the fibrocytes selected were CD45 and collagen I positive. From that population of cells, 93% were IL17RB positive. Mouse and human blood circulating fibrocytes thus expressed IL17RB at comparable levels.

Example 2

Intact IL-25 Signaling in Fibrocytes

The effect of IL-25 on cytokine release in fibrocytes was evaluated to demonstrate functional IL17RB and intact IL-25 signaling pathways in fibrocytes. Specific in vitro stimulation of IL17RB has been shown to increase secretion proinflammatory cytokines in other cell types. IL-25 potentiated TNF-α induced RANTES, IL-6, KC, and CCL2 secretion in fibrocytes, but did not alone stimulate cytokine release.

Figure 1:
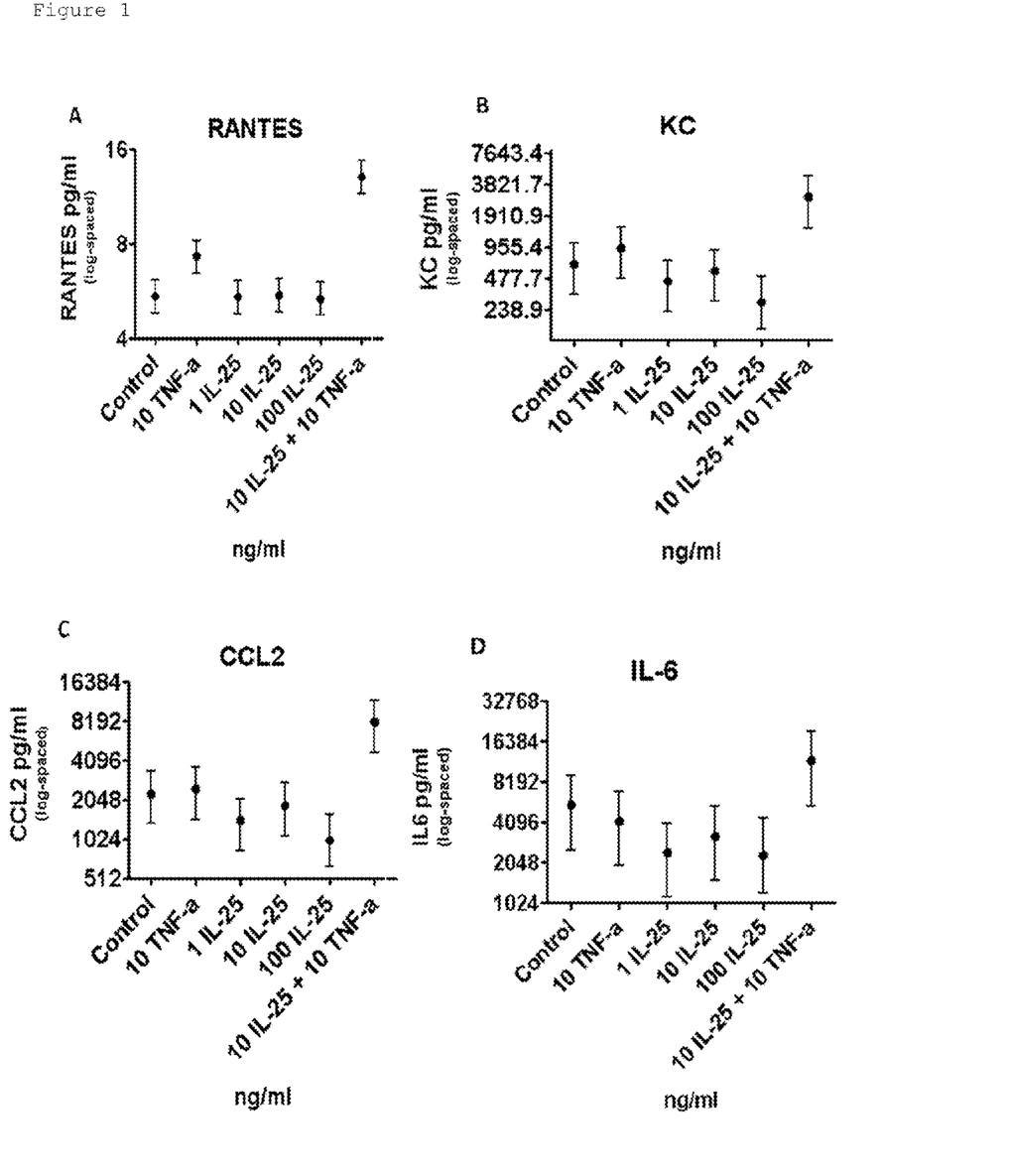
FIG. 1. Cytokine response to IL-25 and IL-25 with TNF-α in fibrocytes. A) RANTES, B) KC, C) CCL2, D) IL-6.

Murine lung fibrocytes (FIG. 1) stimulated with IL-25 alone for 24 hrs did not show an increase in cytokine expression by Luminex. 10 ng/ml of TNF-α alone significantly increased RANTES (FIG. 1A) compared to the control (p=0.022) and to the three concentrations of IL-25 (p=0.021, p=0.025, p=0.018 for 1, 10 and 100 ng/ml of IL-25 respectively), but was significantly lower than IL-25+10 ng/ml TNF-α (p<0.001). Co-stimulation of the fibrocytes with IL-25 and TNF-α resulted in a significant increase in RANTES compared to all of the other groups (p<0.001 for each group). KC (FIG. 1B) was significantly higher for IL-25+10 ng/ml TNF-α compared to the control (p=0.015), to the three concentrations of IL-25 (p=0.004, p=0.009, p=0.001 for 1, 10 and 100 ng/ml of IL-25 respectively) and TNF-α alone (p=0.05). CCL2 (FIG. 1C) was significantly higher for IL-25+10 ng/ml TNF-α compared to the control (p=0.012), to the three concentrations of IL-25 (p=0.002, p=0.005, p<0.001 for 1, 10 and 100 ng/ml of IL-25 respectively), and to TNF-α alone (p=0.017). The change in IL-6 (FIG. 2D) was not found to be significant by a test for an overall difference among all groups (p=0.153), although IL-6 was significantly higher comparing individually 10 ng/ml of IL-25 combined with TNF-α to the three concentrations of IL-25 (p=0.020, p=0.048, p=0.025 for 1 IL-25, 10 IL-25 and 100 IL-25 respectively), but not TNF-α alone.

RANTES is involved in immunoregulatory and inflammatory processes and is transcribed and secreted by T cells, other inflammatory cells and stromal cells. RANTES is a ligand for chemokine receptors CCR1, CCR3, CCR4 and CCR5, which are expressed on epithelial cells, macrophages, lymphocytes, dendritic cells and stromal cells (Ruster et al., Front Biosci. 13:944-55, 2008; van Deventer et al., Cancer Res. 65:3374-9, 2005). CXCL8 is a proangiogenic factor secreted by fibrocytes and is found present during the wound-healing response (Kovacs et al., FASEB J. 8:854-61, 1994). CCL2 is known to be central to the development of pulmonary fibrosis and is involved in the recruitment of fibrocytes to the lung (Moore et al., Am. J. Pathol. 166:675-84, 2005) and is the likely pathway by which it promotes fibrosis. CCL2 secreted by fibrocytes is a potent T cell chemoattractant and may act to specifically recruit CD4$^+$ T cells into the tissue repair environment. IL-6 a hematopoietic growth factor secreted by blood fibrocytes and is active on many cells, including fibroblasts, and it can, therefore, function as an autocrine or paracrine mediator (Moodley et al., Am. J. Pathol. 163:345-54, 2003; Fries et al., Am. J. Respir. Cell Mol. Biol. 11:552-60, 1994). It has been shown to regulate macrophage differentiation, lymphocyte proliferation, Th17 development (Weaver et al., Immunity 24:677-88, 2006), is a pro-fibrogenic factor (Moodley et al., Am. J. Respir. Cell Mol. Biol. 29:490-98, 2003), can inhibit apoptosis in some cells (Liu et al., Am. J. respire. Cell Mol. Biol. 37:121-8, 2007) and is known to be released during early phase of tissue repair (Kishimoto et al., Science 258:593-97, 1992). RANTES, CXCL8 and CCL2 have all been found to be increased in IPF patients and CCL2 has been found elevated in bronchiolar epithelium of chronic obstructive pulmonary disease (COPD) patients (Chung, Curr. Drug Targets Inflamm. Allergy 4:619-25, 2005; Kodama et al., Am. J. Respir. Cell Mol. Boil. 18:526-31, 1998; Tsoutsou et al., Respir. Med. 100:938-45, Epub Oct. 19, 2005).

TNF-α has pleiotropic effects, most of which stimulate an inflammatory response by acting on mononuclear cells, neutrophils, and endothelial cells. In this study, TNF-α was shown to have a co-stimulatory role in fibrocytes with IL-25 to increase secretion of pro-inflammatory cytokines. TNF-α is produced by activated macrophages and lymphocytes, epithelial cells, and endothelial cells. It has a central role in the early events leading to the cytokine and chemokine production cascade. It directly or indirectly stimulates the production of several factors, such as TGF-β, IL-1, IL-6, CXCL8, CCL2, PDGF, and granulocyte-macrophage colony-stimulating factor. A large body of studies on IPF and COPD has demonstrated that this cytokine is present in areas of lung fibrosis (Emad et al., J. Interferon Cytokine Res. 27:38-43, 2007; Chung, Curr. Drug Targets Inflamm. Allergy 4:619-25, 2005. TNF-α has previously been shown in combination with IL-25 in human lung fibroblasts and smooth muscle cells to increase IL17RB mRNA and to induce the expression of proinflammatory cytokines (Letuve et al., J. Allergy Clin. Immunol. 117:590-6, 2006; Lajoie-Kadoch et al., Am. J. Physiol. Lung Cell Mol. Physiol. 290:L1238-46, Epubl Jan. 20, 2006). IL-25 induced intracellular signaling can involve the activation of MAPK family as well as NF-κB (Lee et al., J. Biol. Chem. 276:1660-4, 2001). TNF-α main signaling pathway is also through the NF-κB pathway and thus the overlapping signaling pathways may play a role in the synergistic effect of IL-25 and TNF-α inducing cytokine release in fibrocytes. This suggests that IL-25 and TNF-α could act together in early fibrotic events to drive pro-inflammatory cytokines released from stimulated fibrocytes. Demonstration in this study that fibrocytes have a functional IL17RB may suggest IL-25 acting as a fibrotic mediator through stimulation of circulating and resident fibrocytes.

Example 3

Modulation of IL-25 Signaling Alters Fibrocyte Function

Figure 2A:
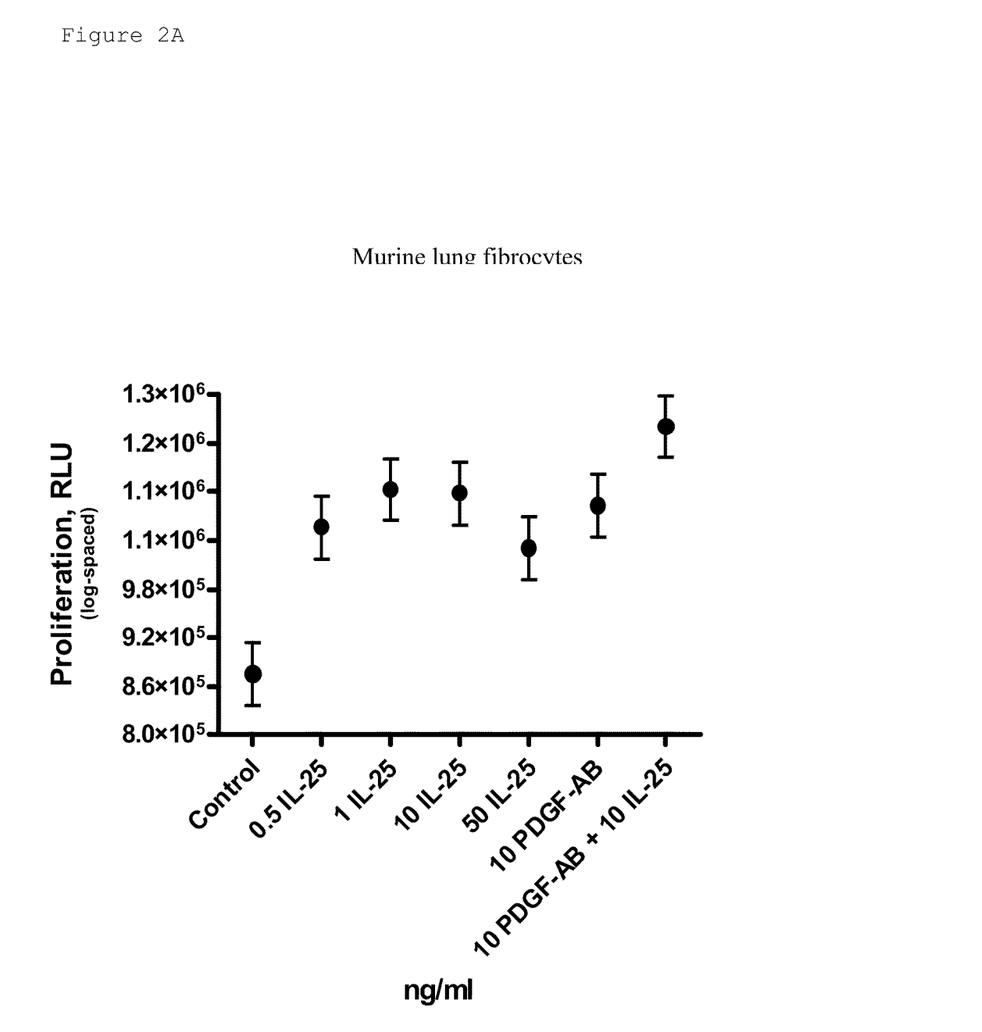
Figure 2B:
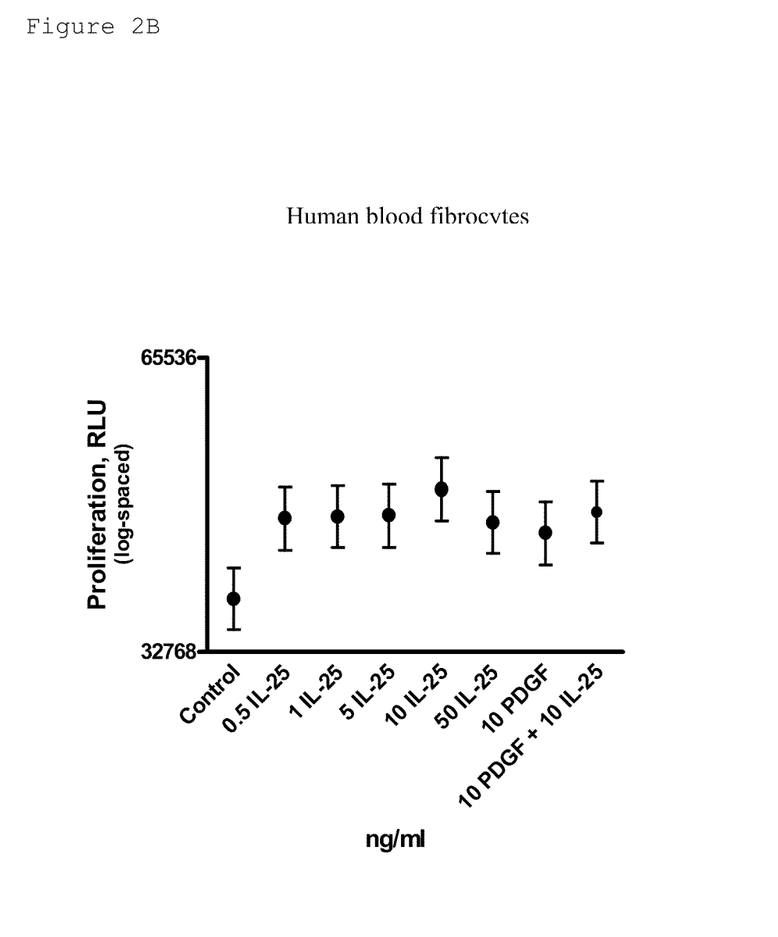

Effect of IL-25 on fibrocyte proliferative capacity was studied by stimulation with IL-25 alone or in combination with PDGF-AB over 96 hrs in serum free medium. PDGF-AB has been shown to enhance in vitro proliferation of lung fibroblasts [27]. PDGF-AB alone caused a 27% increase ($p<0.001$) in murine lung fibrocyte proliferation (FIG. 2A). IL-25 alone significantly increased murine lung fibrocyte proliferation at all tested concentrations ($p<0.001$ for each comparison), with both 1 and 10 ng/ml ($p<0.001$) of IL-25 producing a 30% increase in fibrocyte proliferation (FIG. 2A). The addition of PDGF-AB to murine lung fibrocytes stimulated with IL-25 augmented the increase in proliferative activity compared to either 10 ng/ml of IL-25 ($p=0.04$) or 10 ng/ml of PDGF-AB ($p=0.02$) alone (FIG. 2A). The proliferative effect ($p<0.02$) of PDGF-AB on murine lung fibrocytes was confirmed by BrdU incorporation (data not shown). Thus exogenous IL-25 and/or PDGF-AB can increase murine lung fibrocyte proliferation in vitro. Exogenous addition of IL-25 at 1 ($p=0.006$) and 10 ng/ml ($p=0.001$) also could increase human blood fibrocyte proliferation significantly compared to the serum free control, as did 10 ng/ml PDGF ($p=0.024$) (FIG. 2B).

Figure 2C:
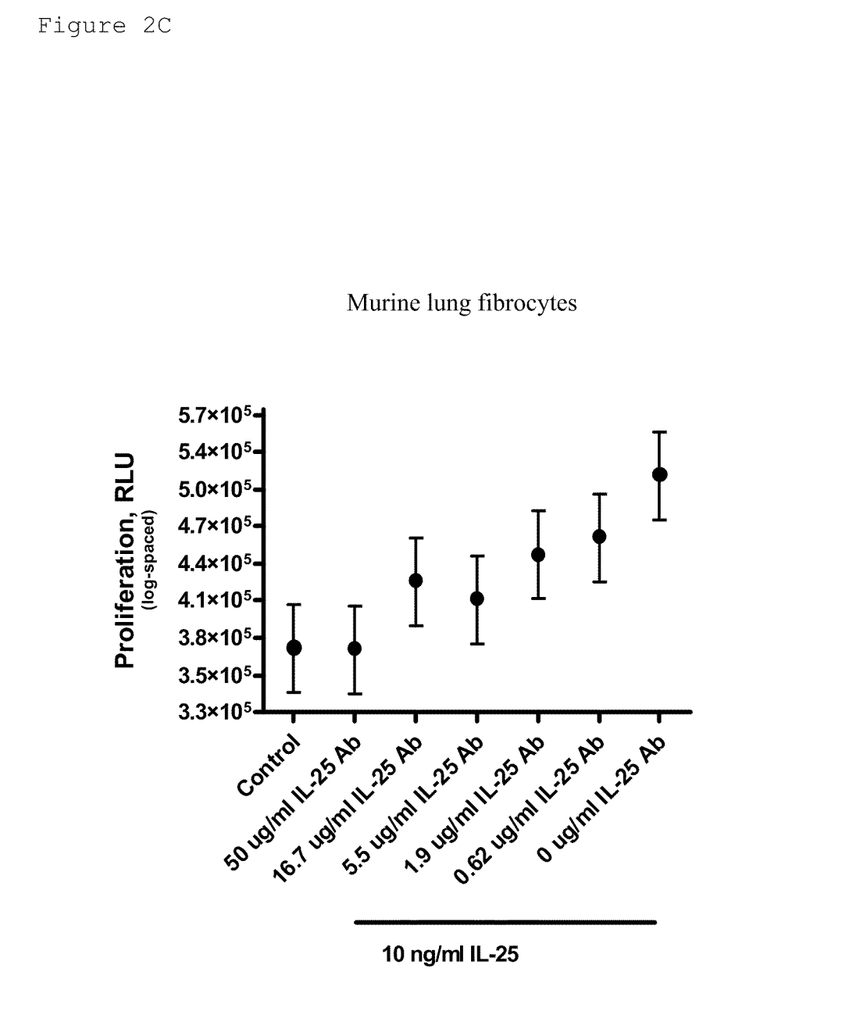
Figure 2D:
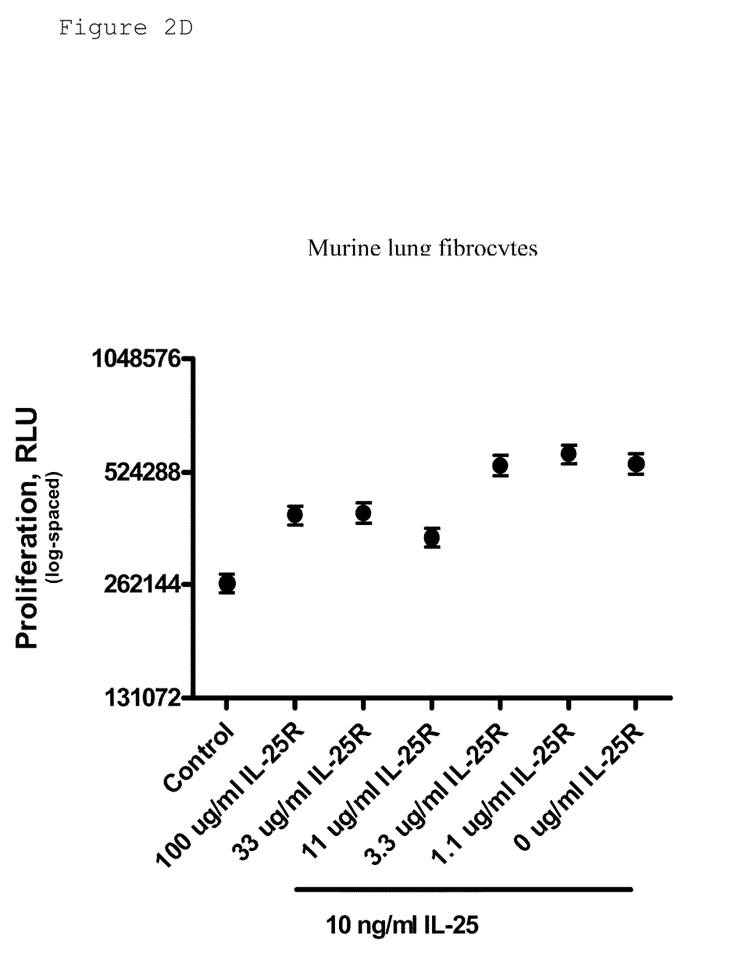

The effect of blocking IL-25 on murine lung fibrocyte proliferation was studied using rat anti-murine IL-25 mAb (mAb 1923). IL-25 induced lung fibrocyte proliferation was significantly reduced with IL-25 mAb concentrations at 5.5 μg/ml ($p=0.011$), 16.7 μg/ml ($p=0.026$) and 50 μg/ml ($p=0.001$) when compared to IL-25 alone (FIG. 2C). To verify the IL-25 response was a proliferative effect not an apoptotic effect on murine lung fibrocytes, BrdU incorporation studies were done in fibrocytes, resulting in a similar response of IL-25 mAb inhibiting IL-25 induced proliferation in the murine lung fibrocytes (data not shown). The rat anti-murine IL-25 mAb produced a significantly linear dose-dependent ($p<0.001$) effect on IL-25 (10 ng/ml) induced murine lung fibrocyte proliferation (FIG. 2B) by reducing proliferation by 3.75% for each 3 fold increase in IL-25 mAb concentration. A significant decrease was also observed in IL-25 (1 ng/ml) induced murine lung fibrocyte proliferation using an IL17RB-Fc chimera at 11 μg/ml or higher ($p<0.001$ for 11, 33 and 100 μg/ml of IL-25R) (FIG. 2D).

Figure 3A:
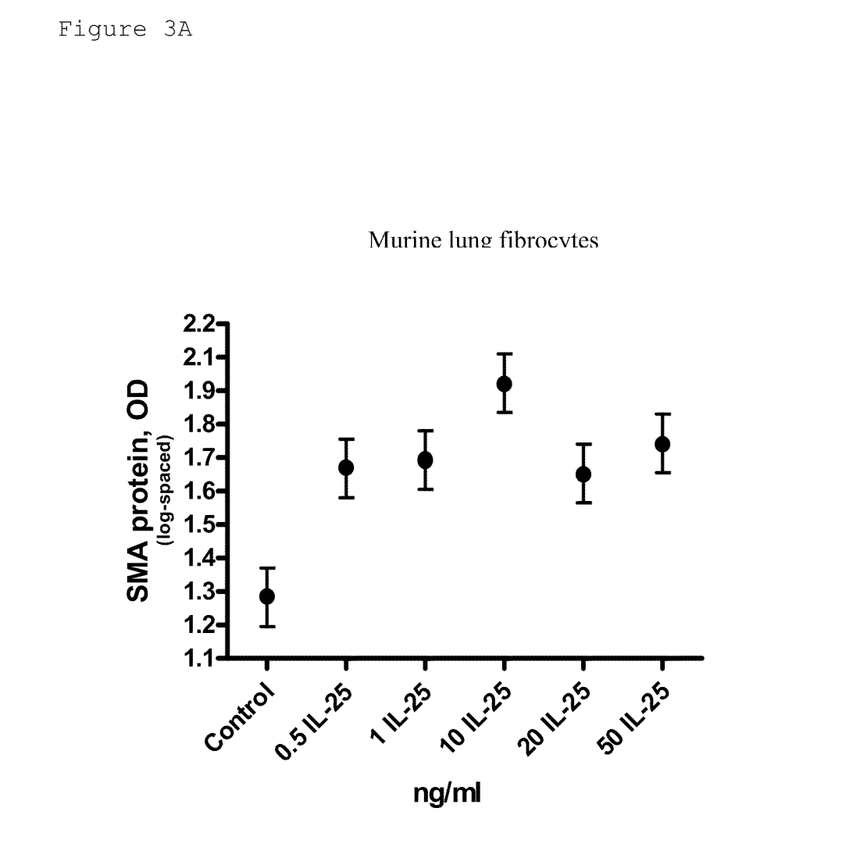
Figure 3B:
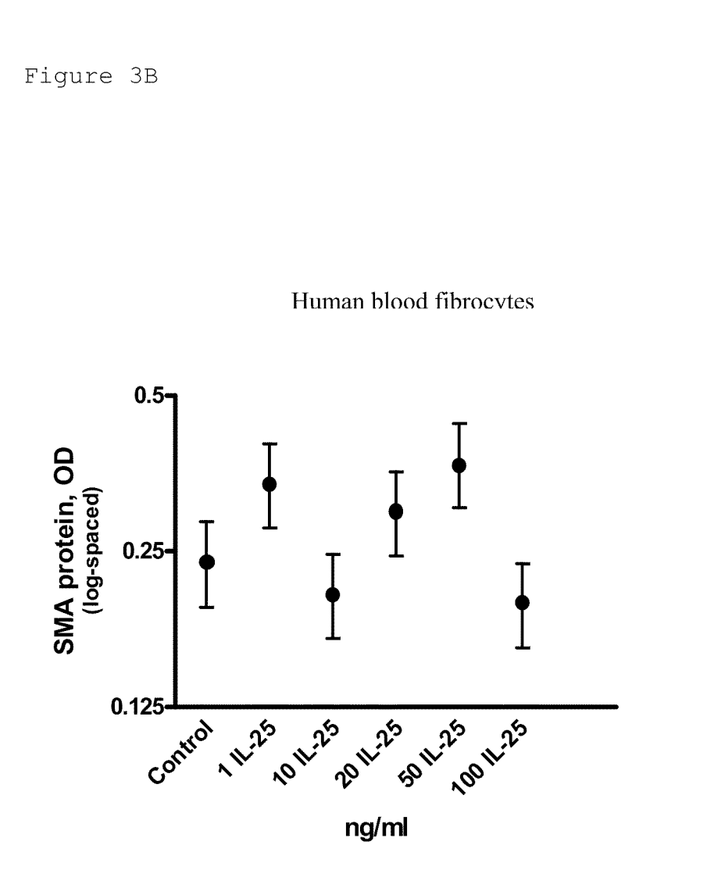
Figure 3C:
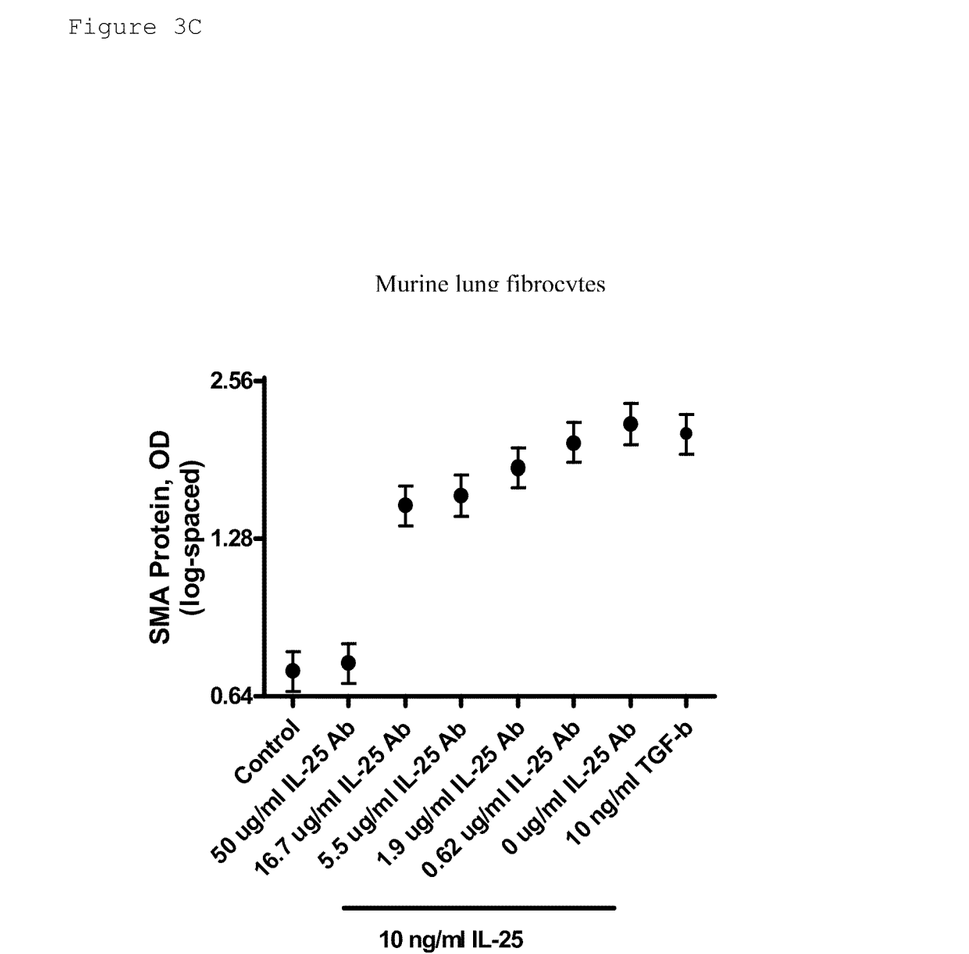

Murine fibrocyte differentiation into myofibroblast-like cells was enhanced due to stimulation with exogenous IL-25 over 96 hrs in serum-free medium. TGF-β, an important fibrogenic and growth-regulating cytokine involved in tissue remodeling, increases the differentiation and functional activity of cultured fibrocytes (Chesney et al., J. Immunol. 160:419-25, 1998; Schmidt et al., J. Immunol. 171:380-9, 2003). Fibrocytes cultured in serum-free media constitutively expressed α-SMA (FIG. 3) and TGF-β treatment increased α-SMA expression in murine lung fibrocytes ($p<0.001$) (FIG. 3C). In murine lung fibrocytes stimulation with IL-25 at all concentrations tested (FIG. 3A) caused significant increases ($p<0.001$) in α-SMA expression compared to the control. Within the IL-25 concentrations assessed, 10 ng/ml of IL-25 caused significantly higher α-SMA expression than 0.5 ng/ml ($p=0.010$), 1 ng/ml ($p=0.017$), and 20 ng/ml ($p=0.007$) of IL-25. IL-25 increased α-SMA expression also in human blood fibrocytes at concentrations of 1, 20, and 50 ng/ml of IL-25, although the increase was only significant for 50 ng/ml IL-25 ($p=0.025$) compared to the serum free control (FIG. 3B).

Effect of blocking IL-25-induced murine lung fibrocyte differentiation was evaluated using a rat anti-murine IL-25 mAb (mAb 1923). The rat anti-murine IL-25 mAb ($p<0.005$) at 50 μg/ml could completely block the murine lung fibrocyte differentiation induced by 10 ng/ml of IL-25 ($p<0.001$ compared to the control) (FIG. 3B). The 50 μg/ml IL-25 mAb group was significantly different than all other IL-25 mAb combinations ($p<0.001$ for each comparison) and the IL-25 alone group ($p<0.001$). The rat ant-murine IL-25 mAb still showed a significant reduction in α-SMA expression compared to the IL-25 alone group at the 16.7 μg/m. IL-25 mAb group ($p=0.001$), 5.5 μg/ml IL-25 mAb group ($p=0.002$) and 1.9 μg/ml IL-25 mAb group ($p=0.040$) concentrations. There was a significant dose-response relationship (FIG. 3C) between IL-25 mAb concentration and α-SMA expression when IL-25 mAb was combined with IL-25. These differentiation studies conducted in mouse and human cells demonstrated that IL-25 could augment fibrocyte differentiation into myofibroblasts and the differentiation could be blocked by an inhibitor of IL-25 signaling.

Methodologies

Fibrocyte isolation from murine lungs and, murine and human peripheral blood.

Murine lungs were removed using aseptic conditions. Pooled lungs were minced with scissors in DMEM complete media containing 20% fetal calf serum. Lungs were placed in 10 ml of media in 100 cm$^2$ tissue culture dish. Nonadherent cells were removed after 3 days and cells were grown for another 4 days in culture when cells reached 80-90% confluence. Cells were harvested using Accutase and stained with anti-CD45 Abs coupled to magnetic beads (Miltenyi Biotech). Labeled cells were then positively sorted one to two times by using autoMacs apparatus according to manufacturer's instructions. Flow cytometry staining on this population confirmed that these cells were CD45$^+$ collagen (col) 1$^+$.

For collection of human blood, all necessary permissions, approvals, and licenses, including approval by a relevant third party Institutional Review Board (IRB) of an Informed Consent Form and Protocol and any relevant study-related documentation required by the IRB, were collected and maintained for the sourcing, handling, storage, banking, transport, or use of biological samples from employee volunteers at Centocor, R&D, Inc. Total PBMCs first were isolated from human or murine blood by centrifugation over Ficoll-Paque (Pharmacia, Uppsala, Sweden) following the manufacturer's protocol. After 2 days in culture on uncoated culture dishes in DMEM (Life Technologies, Gaithersburg, Md.) supplemented with 20% FCS (HyClone Labs, Logan, Utah), the nonadherent cells were removed by a single, gentle aspiration. Following 10 to 12 days of continuous culture, the adherent cells were lifted by incubation in Accutase and were depleted by immunomagnetic selection of contaminating T cells (pan-T, anti-CD2, Miltenyi Biotech), monocytes (anti-CD14, Miltenyi Biotech), and B cells (Pan-B, anti-CD19, Miltenyi Biotech). Cell viability was determined to be >90% by Guava analysis.

Generation of Murine Anti-IL-25 Monoclonal Antibodies

One 12-14 week old CD rat (Charles River Laboratories) received two intraperitoneal (IP) injections of 50 mg murine IL-25 (R&D Systems, Minneapolis, Minn.) emulsified in Titermax adjuvant on days 0 and 14. On day 68, the rat received a final boost of 50 mg murine IL-25 subcutaneous three days prior to splenic harvest for fusion. The spleen was isolated, a single cell suspension prepared and fusion was carried out at a 1:1 ratio of FO murine myeloma cells to viable spleen cells according to the method of De St. Groth [25]. Cell fusion was initiated with PEG 4000 and clones were grown out in the presence HAT medium [DMEM with Glutamax™ (modified), supplemented with 20% FBS, 5% Origen, 25 µg/mL gentamicin (Sigma) and HAT (100 µM hypoxanthine, 0.4 µM aminopterin, and 16 µM thymidine (Sigma) and plated in semi-solid methylcellulose (Medium D, StemCell Technologies) in large Petri dishes (Genetix, Hampshire, United Kingdom). Plates were subjected to the ClonePix™ instrument (Gentix) for single colony selection based on white light images. Single colonies were selected into Medium E (StemCell Technologies) for further testing. Primary screening of all undiluted hybridoma supernatants was performed using a capture IL-25 ELISA. All cell lines that bound recombinant murine IL-25 were subcloned by limiting dilution and screened by both solid and capture IL-25 ELISAs. An IL-25 neutralizing hybridoma clone was identified, expanded and the expressed monoclonal antibody mAb 1923 was purified by flask batch purification.

Immunocytochemistry

For immunofluorescence, cells were seeded into 8 well slides at $1.5 \times 10^4$ cells/well and were fixed when semi-confluent (day 7) in 3% formaldehyde for 10 min at room temperature and washed several times in PBS. The cells were permeablized with methanol for 10 min. at −20° C. and washed in staining buffer, blocked and detected using standard protocols. Primary antibodies used were: rat anti-mouse CD45 monoclonal antibody (1:40 dilution; BD Biosciences, San Jose Calif.), rabbit anti-mouse collagen I polyclonal antibody (1:200 dilution; Chemicon, Temecula, Calif.) or rat anti-mouse IL-25R monoclonal antibody (1:50 dilution; R&D Systems). Isotype controls were: rat $IgG_{2b}$ isotype control (1:320 dilution; BD Biosciences) and rabbit IgG isotype control (1:300 dilution; Imgenex, San Diego, Calif. Secondary antibodies used were Alexa Fluor® 594 goat anti-rat IgG (H+L) (1:250; Molecular Probes, Eugene, Oreg.) or Alexa Fluor® 647 goat anti-rabbit IgG (H+L) (1:200 dilution; Molecular Probes). All slides were viewed on the laser confocal microscope (UltraVIEW ERS spinning disk; Perkin Elmer, Wellesley, Mass.).

Flow Cytometry Analysis

For flow cytometry of murine lung and blood fibrocytes analysis, $2 \times 10^5$ viable cells were added to flow tubes and centrifuged. The cells were resuspended in 50 µl of staining buffer (0.2% BSA and 0.02% Sodium Azide in PBS) and 1 µl of Fc blocker (BD Biosciences) and incubated for 10 min. The PE conjugated anti-CD45 monoclonal antibody (BD Biosciences) was added and incubated for 40 min. after which the cells were washed, fixed and permeabilized in BD cytofix/cytoperm (BD Biosciences) for 20 mins. The cells were resuspended in the BD buffer, and the proteins were detected using rat anti-mouse IL-25R primary antibody (1:50 dilution; R&D systems) and biotin conjugated anti-Collagen I (1:150 dilution; Rockland, Gilbertsville, Pa.) followed by Alexa Fluor® 488 goat anti-rat IgG (1:200 dilution; Molecular Probes) and Streptavidin-Allophycocyanin conjugate (1:150; BD Biosciences). The cells were washed and fixed with 3% paraformaldehyde. Isotype controls were PE conjugated rat $IgG_{2b}$ isotype control (BD Biosciences), rat $IgG_{2b}$ isotype control (R&D Systems) and IgG fraction of anti-Biotin (1:1500; Rockland).

For flow cytometry of human blood fibrocytes $2 \times 10^5$ viable cells were added to flow tubes and centrifuged. The cells were resuspended in 50 µl of staining buffer (0.2% BSA and 0.02% Sodium Azide in PBS) and 1 µl of Fc blocker and incubated for 10 min. The PE conjugated anti-CD45 monoclonal antibody (Clone HI30, eBiosciences, San Diego, Calif.) was added and incubated for 40 min. after which the cells were washed, fixed and permeabilized in BD cytofix/cytoperm (BD Biosciences) for 20 min. The cells were resuspended in the BD buffer, and the proteins were detected using mouse anti-human IL-25R ab (1:100 dilution; R&D systems) and biotin conjugated anti-Collagen I ab (1:150 dilution; Rockland, Gilbertsville, Pa.), followed by Alexa Fluor® 488 goat anti-mouse IgG (1:200 dilution; Molecular Probes) Streptavidin-Allophycocyanin conjugate (1:150 dilution; BD Biosciences). The cells were washed and fixed with 3% paraformaldehyde. Isotype controls were mouse $IgG_1$ isotype control (BD Biosciences), rat $IgG_{2b}$ isotype control (1:320 dilution; BD Biosciences) and IgG fraction of anti-Biotin (1:1500 dilution; Rockland).

Protein Secretion Studies

For protein secretion assay freshly selected murine lung and blood fibrocytes and human blood fibrocytes were plated at $1 \times 10^4$ viable cells/well in a 96 well tissue culture plate. The cells were incubated in control media (10% BSA in DMEM) for 5 days, serum starved for 24 hours, and incubated for 24 hrs in serum free DMEM in the presence of IL-25 or TNF-α alone or IL-25 and TNF-α in combination. Cytokine/chemokine levels were measured in the conditioned medium using a Mouse Cytokine/Chemokine Panel-22 Plex (Millipore, Billerica, Mass.) for murine fibrocytes or Human Cytokine/Chemokine Panel-25 Plex (Millipore) for human fibrocytes and analyzed on the Luminex System. Data are expressed as the mean±SD (n=2).

Cell Proliferation Assay

For cell proliferation assay freshly selected murine lung fibrocytes or human blood fibrocytes were plated at $0.5 \times 10^4$ viable cells/well in a 96 well tissue culture plate. The cells were incubated in control media (10% BSA in DMEM) overnight. The media was removed and replaced with IL-25 or PDGF-AB alone or IL-25 and PDGF-AB in combination in serum free media (1% BSA and ITS in DMEM. mAb 1923 was used at concentrations between 0.62-50 µg/ml, and the recombinant mature human IL-25RFc chimera (R&D systems) was used at concentrations between 1.1-100 µg/ml. The IL-25RFc or the mAb 1923 was incubated with IL-25 for 40 min. before being added to the fibrocyte cells. Cell proliferation was measured using CellTiter-Glo® (Promega, Madison Wis.) and BrdU incorporation. Data are expressed as the mean±SD (n=3).

Differentiation Assay

For cell differentiation assay freshly selected murine lung fibrocytes or human blood fibrocytes were plated at $1.5 \times 10^4$ viable cells/well in an opaque 96 well tissue culture plate. The cells were incubated in control media (10% BSA in DMEM) overnight. The media was removed and replace with IL-25 or TGF-β alone in serum free media (1% BSA and ITS in DMEM). mAb 1923 was used at concentrations between 0.62-50 µg/ml, and was incubated with IL-25 for 40 min before being added to the fibrocyte cells. The cells were incubated for 96 hrs at 37° C., fixed in 100% methanol, blocked and stained with anti-α-smooth muscle actin (1:400 dilution; Sigma) followed by HRP-conjugated anti-mouse IgG (1:2000 dilution; Sigma) for 60 min at room temperature.

The optical density of the wells were analyzed using a plate reader at wavelength of 405 nm. Data are expressed as the men±SD (n=3).

The invention claimed is:

1. A method of suppressing fibrocyte proliferation, fibrocyte differentiation, or protein secretion by the fibrocyte induced by IL-25 in a subject having a condition associated with undesired fibrocyte proliferation, fibrocyte differentiation, or protein secretion by the fibrocyte comprising administering to the subject a therapeutically effective amount of an inhibitor of IL-25 signaling, wherein the inhibitor of IL-25 signaling is an antibody that specifically binds IL-25 and the condition is systemic sclerosis, nephrogenic systemic fibrosis, or graft versus host disease.

2. A method of suppressing fibrocyte proliferation, fibrocyte differentiation, or protein secretion by the fibrocyte induced by IL-25 in a subject having a condition associated with undesired fibrocyte proliferation, fibrocyte differentiation, or protein secretion by the fibrocyte comprising administering to the subject a therapeutically effective amount of an inhibitor of IL-25 signaling, wherein the inhibitor of IL-25 signaling is an antibody that specifically binds IL-25 and the condition is cancer.

3. The method of claim 2, wherein the cancer is breast cancer, skin cancer, pancreatic cancer, or cervical cancer.

4. A method of suppressing fibrocyte proliferation, fibrocyte differentiation, or protein secretion by the fibrocyte induced by IL-25 in a subject having a condition associated with undesired fibrocyte proliferation, fibrocyte differentiation, or protein secretion by the fibrocyte comprising administering to the subject a therapeutically effective amount of an inhibitor of IL-25 signaling, wherein the inhibitor of IL-25 signaling is an antibody that specifically binds IL-25 and the condition is Crohn's disease, chronic cystitis, an autoimmune disease, rheumatoid arthritis, lyme disease, post surgery scarring, wound healing, or radiation damage.

* * * * *